United States Patent
Wu et al.

(10) Patent No.: US 8,273,930 B2
(45) Date of Patent: Sep. 25, 2012

(54) PROCESS FOR PRODUCING ETHYLENE FROM ETHANOL COMBINING THE CATALYTIC CONVERSION OF HYDROCARBONS

(75) Inventors: Zhiguo Wu, Beijing (CN); Wenhua Xie, Beijing (CN); Chaogang Xie, Beijing (CN); Qiang Liu, Beijing (CN); Xuhong Mu, Beijing (CN); Jiushun Zhang, Beijing (CN); Yibin Luo, Beijing (CN); Xingtian Shu, Beijing (CN); Chenghan Yan, Beijing (CN)

(73) Assignees: China Petroleum & Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 323 days.

(21) Appl. No.: 12/373,585

(22) PCT Filed: Jul. 12, 2007

(86) PCT No.: PCT/CN2007/002133
§ 371 (c)(1),
(2), (4) Date: Jan. 13, 2009

(87) PCT Pub. No.: WO2008/009217
PCT Pub. Date: Jan. 24, 2008

(65) Prior Publication Data
US 2009/0281363 A1    Nov. 12, 2009

(30) Foreign Application Priority Data
Jul. 13, 2006  (CN) .......................... 2006 1 0091073

(51) Int. Cl.
*C07C 1/24* (2006.01)

(52) U.S. Cl. .............. 585/324; 208/49; 208/67; 208/78; 585/301; 585/304; 585/312; 585/313; 585/314; 585/315; 585/638; 585/639; 585/640; 585/648; 585/653

(58) Field of Classification Search .................. 585/311, 585/312, 313, 314, 315, 324, 638, 639, 640, 585/648, 653, 301, 304; 208/44, 49, 57, 208/67, 78
See application file for complete search history.

(56) References Cited

U.S. PATENT DOCUMENTS
3,702,886 A    11/1972  Argauer et al.
(Continued)

FOREIGN PATENT DOCUMENTS
CN    1504542 A    6/2004

OTHER PUBLICATIONS
Communication from European Patent Office with an European Search Report, Apr. 29, 2011.
(Continued)

*Primary Examiner* — In Suk Bullock
*Assistant Examiner* — Bradley Etherton
(74) *Attorney, Agent, or Firm* — Anova Law Group, PLLC; Zhi Yang Xue

(57) ABSTRACT

A process for producing ethylene from ethanol combining the catalytic conversion of hydrocarbons: an ethanol feedstock is contacted with a Y-zeolite containing catalyst to give a product stream, and a coked catalyst and an target product of ethylene are obtained after separating the reaction stream; a hydrocarbon feedstock is contacted with a Y-zeolite containing catalyst to give a product stream, a spent catalyst and an oil vapor are obtained after separating the reaction stream, and the oil vapor is further separated to give the products such as gas, gasoline and the like; a part or all of the coked catalyst and a part or all of the spent catalyst enter the regenerator for the coke-burning regeneration, and the regenerated catalyst is divided into two portions, wherein one portion returns to be contacted with the hydrocarbon feedstock, and the other portion, after cooling, returns to be contacted with ethanol feedstock. This process not only reasonably utilizes the excessive thermal energy of the hydrocarbon conversion, but also solves the problem of heat supply for the conversion of ethanol, thus ensuring the continuous catalytic conversion of ethanol and generating enormous economic benefits. For the catalytic conversion of the ethanol, the content of ethylene is 95 vol % or more in the gas product; and the conversion of ethylene is not less than 99%. For the catalytic conversion of the hydrocarbons, the yield for the light olefins increases slightly by at least 2 mol %.

26 Claims, 1 Drawing Sheet

U.S. PATENT DOCUMENTS

| | | | |
|---|---|---|---|
| 3,969,426 A | | 7/1976 | Owen et al. |
| 4,148,835 A | | 4/1979 | Chen et al. |
| 4,251,677 A | * | 2/1981 | Coutinho et al. ............. 585/639 |
| 5,232,675 A | | 8/1993 | Shu et al. |
| 5,481,057 A | | 1/1996 | Bell et al. |
| 5,914,433 A | | 6/1999 | Marker |
| 6,049,017 A | | 4/2000 | Vora et al. |
| 6,303,839 B1 | | 10/2001 | Marker |
| 6,441,261 B1 | | 8/2002 | Kuechler et al. |
| 2005/0020867 A1 | * | 1/2005 | Xie et al. ...................... 585/651 |
| 2007/0007176 A1 | * | 1/2007 | Pinho et al. ................... 208/108 |

OTHER PUBLICATIONS

Communication from European Patent Office with a Supplementary European Search Report re EP 07 76 4039, Aug. 3, 2011.

* cited by examiner

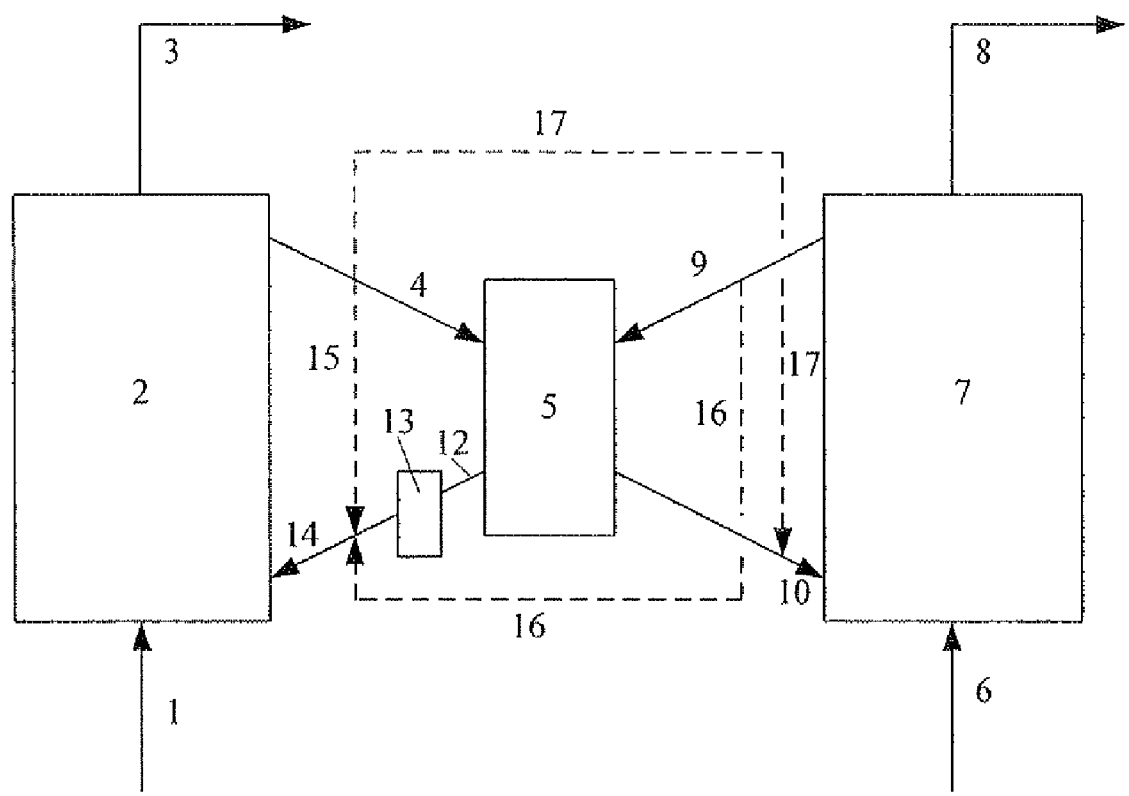

PROCESS FOR PRODUCING ETHYLENE FROM ETHANOL COMBINING THE CATALYTIC CONVERSION OF HYDROCARBONS

FIELD OF THE INVENTION

The present invention relates to a process for producing ethylene from ethanol, more particular, to a process for producing ethylene from ethanol combining the catalytic conversion of hydrocarbons.

BACKGROUND OF THE INVENTION

The global petroleum supply-demand contradiction is increasingly prominent at the beginning of the $21^{st}$ century. Along with the increased demand for various petroleum and petrochemical products, the price of crude oil in the market is continuously increased. This situation leads to persisting high market-prices of important chemical products such as light olefins (especially ethylene and propylene) and light ethers (such as dimethyl ether, ethyl ether, etc), using petroleum and petrochemical products as feedstock. Therefore, it is one choice of solving these problems to seek for another substituting feedstock such as by-product ethanol from agriculture and forestry, and methanol prepared from natural gas or coal to produce light olefins and light ethers.

The process for preparing ethylene from ethanol is to carry out the dehydration reaction $CH_3CH_2OH \rightarrow CH_2=CH_2 + H_2O$ at 140-400° C. with a suitable catalyst. At the beginning of 1980's, India and Brazil built up industry-scale devices for converting ethanol to ethylene, using $SiO_2$—$Al_2O_3$ as catalyst and adopting fixed bed and fluidized bed reactors altogether For the balance of heat, an additional fuel will be added when the catalyst is regenerated.

The process disclosed in U.S. Pat. No. 6,441,261 is to convert oxygenates (methanol, etc) to light olefins, e.g. ethylene and propylene, on a silicoaluminophosphate molecular sieve catalyst under a relative high pressure.

U.S. Pat. No. 6,303,839 and U.S. Pat. No. 5,914,433 convert oxygenates (methanol, etc) to light olefins and fractionate out the propylene and/or butene therein for cracking, thereby enhancing the yield of ethylene and propylene. Although the above processes also use fluidized bed operation, it is seen from the data of the examples that the yield of coke is only 2%. With a low yield of coke, the heat of the system is difficult to be balanced, and an external heat supply is generally needed.

U.S. Pat. No. 6,049,017 increases the yield of light olefins by separating the product containing $C_4$ components and converting them to ethylene and propylene on a non-molecular sieve catalyst. This process may be used in the catalytic cracking or the methanol dehydration for producing ethylene and propylene.

U.S. Pat. No. 4,148,835 uses a shape-selective molecular sieve catalyst and derivatives thereof to convert alcohols (especially methanol) to a product mainly containing light olefins, but this patent does not mention of the process.

The ethanol dehydration reaction is an endothermic reaction, and is conducted at a certain temperature. Although coke deposition may occur during the reaction, the amount of the coke is insufficient to balance the heat of the process. In summary, all the prior arts provide the heat in a manner of supplying an external fuel, making the process too complicated or the energy consumption too high.

SUMMARY OF THE INVENTION

Based on the prior art, the object of the present invention is to provide a process for producing ethylene from ethanol combining the catalytic conversion of hydrocarbons.

According to the present invention, the process for producing ethylene from ethanol combining the catalytic conversion of hydrocarbons comprises the following steps:

(1) An ethanol feedstock is contacted with a Y-zeolite containing catalyst to give a product stream, and a coked catalyst and a target product of ethylene are obtained after separating the reaction stream;

(2) A hydrocarbon feedstock is contacted with a Y-zeolite containing catalyst to give a product stream, a spent catalyst and an oil vapor are obtained after separating the reaction stream, and the oil vapor is further separated to give the products such as gas, gasoline and the like;

(3) A part or all of the coked catalyst in step (1) and a part or all of the spent catalyst in step (2) enter a regenerator for the coke-burning regeneration, and the regenerated catalyst is divided into two portions, wherein one portion returns to step (2), and the other portion returns to step (1) after cooling.

The ethanol content in the ethanol feedstock in the present invention is 50-100 wt %, preferably 70-100 wt %, and more preferably 90-100 wt %. A small amount of impurities such as water and methanol may be contained in the ethanol feedstock.

Said hydrocarbon feedstock is selected from the group consisting of $C_4^+$ hydrocarbons, crude oil, gasoline, diesel oil, vacuum gas oil, coker gas oil, deasphalted oil, hydrogenated bottom, atmospheric residuum, vacuum residuum and mixtures thereof; and it is preferably selected from the group consisting of vacuum gas oil, coker gas oil, deasphalted oil, hydrogenated bottom, atmospheric residuum, vacuum residuum and mixtures thereof.

Said Y-zeolite containing catalyst may contain a Y-zeolite and an optional other molecular sieve, but not contain inorganic oxides and clay, wherein the weight ratio of the other molecular sieve to the Y-zeolite is 0-10. Said Y-zeolite containing catalyst preferably contains inorganic oxides and/or clay, a Y-zeolite, and an optional other molecular sieve, wherein the weight ratio of the other molecular sieve to the Y-zeolite is 0-10, and the total weight of the other molecular sieve and the Y-zeolite comprises 10-60% of the catalyst.

Said Y-zeolite includes Y-type zeolite and their derivative or modified zeolites, and is selected from the group consisting of Y, HY, REY, REHY, USY, REUSY and mixtures thereof.

Said other molecular sieve is one or more selected from meso porous zeolites, Beta-zeolites, and SAPO-molecular sieves.

Said meso porous zeolite includes ZRP series (rare earth-modified), ZSP series (iron-modified), ZSM series zeolites and their derivative or modified zeolites. For the more detailed description of ZRP, a reference may be made to U.S. Pat. No. 5,232,675. Said ZSM series zeolite is selected from the group consisting of ZSM-5, ZSM-11, ZSM-12, ZSM-22, ZSM-23, ZSM-35, ZSM38, ZSM-48, and other zeolites having a similar structure. For more detailed description of ZSM-5, a reference may be made to U.S. Pat. No. 3,702,886.

A more preferred Y-zeolite containing catalyst contains Y-zeolites, meso porous zeolites, inorganic oxides, and clay, wherein the weight ratio of the meso porous zeolite to the Y-zeolite is 0.1-10, and the total weight of the meso porous zeolite and the Y-zeolite accounts for 10-60% of total weight of the catalyst.

Said inorganic oxide is selected from the group consisting of alumina, silica, amorphous silica-alumina and mixtures thereof The clay is kaolin and/or halloysite.

The reaction conditions in step (1) are a temperature of 200-450° C., preferably 250-400° C., a pressure (gauge) of 0-0.8 MPa, a weight ratio of the catalyst to the ethanol feedstock of 0.05-20, and a weight hourly space velocity of 0.05-10 $h^{-1}$, preferably 0.1-5 $h^{-1}$.

The reaction conditions in step (2) are a temperature of 400-700° C., preferably 450-600° C., a pressure (gauge) of 0-0.8 MPa, a weight ratio of the catalyst to the hydrocarbon feedstock of 1-30, and a contact time of 1-10 seconds.

The catalytic conversion process in step (2) comprises conventional catalytic cracking processes and various family processes such as the DCC process, CPP process, MIP process, MIP-CGP process, MGD process, MGG process, ARGG process, SHMP process and the like.

The proportion of the coked catalyst in step (1) subjected to coke-burning is 0.5-100%, preferably 5-60%, more preferably 8-40% by the total weight of the coked catalyst. When a portion of the coked catalyst in step (1) enters the regenerator for the coke-burning regeneration, the remaining coked catalyst returns to step (1) and/or step (2), and said portion of the coked catalyst subjected to coke-burning comprises 0.5-99%, preferably 5-60%, more preferably 8-40% by the total weight of the coked catalyst.

The proportion of the spent catalyst in step (2) subjected to coke-burning is 1-100%, preferably 50-100%, more preferably 80-100% by the total weight of the spent catalyst. When a portion of the spent catalyst in step (2) enters the regenerator for the coke-burning regeneration, the remaining spent catalyst returns to step (1), and said portion of the spent catalyst comprises 1-99%, preferably 50-99%, more preferably 80-99% by the total weight of the spent catalyst.

The regeneration in step (3) is one-stage regeneration or two-stage regeneration, and said regenerated catalyst is a partially regenerated catalyst (i.e. semi-regenerated catalyst) and/or a full regenerated catalyst. The weight ratio of the coked catalyst and the spent catalyst entering the regenerator for the coke-burning regeneration is no more than 1.0, preferably no more than 0.5, more preferably no more than 0.2.

The reactors used in step (1) and step (2) are both catalyst-movable reactors, and are selected from the group consisting of a fluidized bed, a riser, a descending transfer line reactor, a moving bed, a composite reactor of riser and fluidized bed, a composite reactor of riser and descending transfer line, a composite reactor of two or more risers, a composite reactor of two or more fluidized beds, a composite reactor of two or more descending transfer lines, and a composite reactor of two or more moving beds. Each of the above reactors may be divided into two or more reaction zones. The preferred reactor in step (1) is a fluidized bed, more preferably a dense-phase fluidized bed. The preferred reactor in step (2) is a riser Said riser is one or more selected from an iso-diameter riser, an equal-velocity riser, and various variable-diameter risers. Said fluidized bed is one or more selected from a fixed fluidized bed, a particulate fluidization bed, a bubbling bed, a turbulent bed, a quick bed, a transfer bed, and a dense-phase fluidized bed.

An existing catalytic cracking reactor may be used as the aforesaid reactor. Alternatively, a necessary modification may be made to an existing catalytic cracking reactor. Also the reactors having a similar structure and function to an existing catalytic cracking reactor can be used.

The product separation device may be the same one shared in Step (1) and Step (2), or the product separation device used in Step (1) is different from that in Step (2). The excessive ethanol separated in step (1) may return to step (1). The $C_4^+$ light hydrocarbons separated in step (2) may return to step (1) and/or step (2).

The regenerated catalyst returning to the reactor of step (1) is first cooled down to 200-450° C. in a direct heat exchange mode or an indirect heat exchange mode. The direct heat exchange mode is to carry out heat exchange by directly contacting the regenerated catalyst with the air having a relatively low temperature. The air is a part or all of the air compressed by an air compressor and delivered to the regenerator, that is, the high temperature thermal energy from a portion of regenerated catalyst is used to preheat the air entering the regenerator. The direct heat exchanger is in a type of fluidized bed or riser, and the cooled catalyst separated by a cyclone separator enters the catalytic conversion reactor of ethanol after stripping off the gas impurities (nitrogen, oxygen, carbon dioxide and the like) with the hot steam. The indirect heat exchange mode is to use an indirect heat exchanger, wherein the hot catalyst passes through the tube side and the steam passes through the shell side.

The process for producing ethylene from ethanol combining the catalytic conversion of hydrocarbons according to the present invention, not only reasonably utilizes the excessive thermal energy of the hydrocarbon conversion, but also solves the problem of heat supply for the conversion of ethanol, thus ensuring the continuous catalytic conversion of ethanol and generating enormous economic benefits. For the catalytic conversion of the ethanol, the content of ethylene is 95 vol % or more in the gas product; and the conversion of ethylene is not less than 99%. For the catalytic conversion of the hydrocarbons, the yield for the light olefins increases slightly by at least 2 mol %.

BRIEF DESCRIPTION OF THE DRAWINGS

FIG. 1 is a schematic flowsheet of the process for producing ethylene from ethanol combining the catalytic conversion of hydrocarbons according to an embodiment of the present invention.

PREFERRED EMBODIMENTS OF THE INVENTION

The process of the present invention will be further illustrated in reference to the drawing, but the present invention is not limit thereto.

FIG. 1 is a schematic flowsheet of the process for producing ethylene from ethanol combining the catalytic conversion of hydrocarbons according to an embodiment of the present invention.

An ethanol feedstock from line 1 is introduced into the reactor 2 and contacted with a Y-zeolite containing regenerated catalyst from line 14 to react at 200-450° C., under a pressure (gauge) of 0-0.8 MPa, at a weight ratio of the catalyst to ethanol feedstock of 0.05-20, with a weight hourly space velocity of 0.1-10 $h^{-1}$. A coked catalyst and a product stream are obtained after separating the reaction stream. The product stream is withdrawn through the line 3 and further separated to give the target product of ethylene. The coked catalyst may be partially or completely introduced into the regenerator 5 through the line 4 for the coke-burning regeneration, and a portion of the coked catalyst may return to the reactor 2 sequentially through the lines 15 and 14 or return to the reactor 7 sequentially through the lines 17 and 10.

The hydrocarbon feedstock from line 6 is introduced into the reactor 7 and contacted with a Y-zeolite containing regenerated catalyst from the line 10 to react at 400-700° C., under a pressure (gauge) of 0-0.8 MPa, at a weight ratio of the catalyst to the hydrocarbon feedstock of 1-30, with a contact time of 1-10 s. A spent catalyst and an oil vapor are obtained after separating the reaction stream, wherein the oil vapor is withdrawn through the line 8 and further separated to give the products such as gas, gasoline, diesel oil and the like (not shown in the figure). After stripping, the spent catalyst is completely or partially introduced into the regenerator 5 through the line 9 for the coke-burning regeneration, and a portion of the spent catalyst may return to the reactor 2 sequentially through the lines 16 and 14.

The weight ratio of the coked catalyst and the spent catalyst entering the regenerator 5 for the coke-burning regeneration is no more than 1.0, preferably no more than 0.5, more preferably no more than 0.2. The regenerated catalyst, which is coke-burning regenerated in the regenerator 5, is divided into two portions, wherein one portion returns to the reactor 7 through line 10, and the other portion sequentially enters the heat exchanger 13 through the line 12, cools therein, and then returns to the reactor 2 through the line 14.

The process of the present invention will further be illustrated by the following examples, but the present invention is not limit thereto.

EXAMPLE 1

The ethanol feedstock and hydrocarbon feedstock used in this example were an ethanol feedstock containing 95% ethanol brewed from grains and vacuum gas oil (VGO), respectively, and the properties of VGO are shown in Table 1. The catalyst used in this example was CGP-1 (containing 25 wt % of REY-zeolite, 10 wt % of ZSP-zeolite, and the balanced support, all based on the total weight of the catalyst) produced by SINOPEC Catalyst Company Qilu Division.

The ethanol feedstock was introduced into a fluidized bed reactor and contacted with the CGP-1 catalyst to react at 340° C., under a pressure (gauge) of 0.1 MPa, at a weight ratio of the catalyst to the ethanol feedstock (catalyst/alcohol ratio) of 1, with a weight hourly space velocity of 1.0 h$^{-1}$. A coked catalyst and a product stream were obtained after separating the product stream. The product stream was further separated to give the target product of ethylene. The product distribution is shown in Table 2. The coked catalyst was divided into two portions, wherein 20 wt % of the coked catalyst was introduced into the regenerator for the coke-burning regeneration, and the remaining 80 wt % of the coked catalyst retuned to the fluidized bed reactor through the inner recycle.

The preheated VGO was injected into a riser reactor after the steam atomization at a weight ratio of the steam to VGO was 0.1:1. VGO was contacted with the hot CGP-1 catalyst in the riser to react at 500° C., under a pressure (gauge) of 0.1 MPa, at a weight ratio of the catalyst to VGO (catalyst/oil ratio) of 6, with a reaction time of 3 seconds. The mixture of the oil vapor and the catalyst rose along the riser to the outlet of the riser. The reaction product and the spent catalyst were separated. The reaction product was introduced into the settler and then into the subsequent separation system to further separate into various products. The product distribution is shown in Table 2. The spent catalyst entered the stripper under the action of gravity to strip with the steam, and it was then introduced into the regenerator for the coke-burning regeneration.

20 wt % of the coked catalyst and all the spent catalyst were regenerated in the regenerator, wherein the weight ratio of the coked catalyst and the spent catalyst entering the regenerator for the coke-burning regeneration is about 0.02. After the regeneration, the regenerated catalyst were divided into two portions, wherein 85 wt % of the regenerated catalyst, having a temperature of 660° C., retuned to the riser for the recycling use, and the remaining 15 wt % of the regenerated catalyst was cooled down to 410° C. and retuned to the fluidized bed for the recycling use.

The testing results demonstrated that by combining the catalytic conversion of ethanol and the catalytic conversion of hydrocarbons, the heat between the two conversions can be balanced, and there is no need for the external fuel or other heat sources. For the catalytic conversion of the ethanol, the content of ethylene is as high as 95.79 vol % in the gas product; and the conversion of ethylene is as high as 99%.

Further, the inventors also found that:

(1) The catalytic conversion of ethanol had not any effect on the crystalline phase of the catalyst CGP-1; and in comparison of the catalyst's acidity prior to the catalytic conversion, the catalyst's acidity decreased slightly after the catalytic conversion; and (2) For the catalytic conversion of the hydrocarbons, the yield for the light products increases slightly by 2 mol % by combining the catalytic conversion of ethanol and the catalytic conversion of the hydrocarbons, the reason for which is believed that the catalyst's acidity is decreased.

EXAMPLE 2

In this example, the ethanol feedstock is identical to that of Example 1; and the hydrocarbon feedstock is an atmospheric residuum. The properties of the atmospheric residuum are shown in Table 1. The catalyst used in this example was MMC-2 (containing 10 wt % of USY-zeolite, 20 wt % of ZSM-5 zeolite, and the balanced support, all based on the total weight of the catalyst) produced by SINOPEC Catalyst Company Qilu Division.

The ethanol feedstock was introduced into a fluidized bed reactor and contacted with the MMC-2 catalyst to react at 360° C., under a pressure (gauge) of 0.1 MPa, at a weight ratio of the catalyst to the ethanol feedstock (catalyst/alcohol ratio) of 5, with a weight hourly space velocity of 1.5 h$^{-1}$. A coked catalyst and a product stream were obtained after separating the reaction stream. The product stream was further separated to give the target product of ethylene. The product distribution is shown in Table 2. The coked catalyst was divided into two portions, wherein 30 wt % of the coked catalyst was introduced into the regenerator for the coke-burning regeneration, and the remaining 70 wt % of the coked catalyst retuned to the fluidized bed reactor through the inner recycle.

The preheated atmospheric residuum was injected into a riser reactor after the steam atomization at a weight ratio of the steam to the atmospheric residuum was 0.1:1. The atmospheric residuum was contacted with the hot MMC-2 catalyst in the riser to react at 550° C., under a pressure (gauge) of 0.1 MPa, at a weight ratio of the catalyst to the atmospheric residuum (catalyst/oil ratio) of 8, with a reaction time of 4 seconds. The mixture of the oil vapor and the catalyst rose along the riser to the outlet of the riser. The reaction product and the spent catalyst were separated. The reaction product was introduced into the settler and then into the subsequent separation system to further separate into various products. The product distribution is shown in Table 2. The spent catalyst entered the stripper under the action of gravity to strip with the steam, and it was then introduced into the regenerator for the coke-burning regeneration.

30 wt % of the coked catalyst and all the spent catalyst were regenerated in the regenerator, wherein the weight ratio of the coked catalyst and the spent catalyst entering the regenerator for the coke-burning regeneration is about 0.02. After the regeneration, the regenerated catalyst were divided into two portions, wherein 80 wt % of the regenerated catalyst, having a temperature of 680° C., retuned to the riser for the recycling use, and the remaining 20 wt % of the regenerated catalyst was cooled down to 410° C. and retuned to the fluidized bed for the recycling use.

The testing results demonstrated that by combining the catalytic conversion of ethanol and the catalytic conversion of hydrocarbons, the heat between the two conversions can be balanced, and there is no need for the external fuel or other heat sources. For the catalytic conversion of the ethanol, the content of ethylene is as high as 98.3 vol % in the gas product; and the conversion of ethylene is as high as 99.1%.

Further, the inventors also found that:

(1) The catalytic conversion of ethanol had not any effect on the crystalline phase of the catalyst MMC-2; and in comparison of the catalysts acidity prior to the catalytic conversion, the catalyst's acidity decreased slightly after the catalytic conversion; and (2) For the catalytic conversion of the hydrocarbons, the yield for the light products increases slightly by 2 mol % by combining the catalytic conversion of ethanol and the catalytic conversion of the hydrocarbons, the reason for which is believed that the catalyst's acidity is decreased.

TABLE 1

| Feedstock Properties | VGO | Atmospheric residuum |
|---|---|---|
| Density (20° C.), g/cm³ | 0.9526 | 0.9387 |
| Sulfur content, ppm | 11000 | 12000 |
| Nitrogen content, ppm | 916 | 647 |
| Carbon residue, m % | 12.4 | 9.2 |
| C, m % | 86.3 | 85.95 |
| H, m % | 11.52 | 11.83 |
| Kinetic viscosity, mm²/s | | |
| 80° C. | 1102.3 | 325.1 |
| 100° C. | 650.7 | 129.5 |
| Freezing point, ° C. | 45 | 35 |
| True boiling point, ° C. | >450 | >350 |
| Vanadium, ppm | 2.1 | 1.7 |
| Nickel, ppm | 42 | 30 |

TABLE 2

| | Example 1 | Example 2 |
|---|---|---|
| Catalyst type | CGP-1 | MMC-2 |
| Catalytic conversion of ethanol | | |
| Reaction conditions | | |
| Temperature, ° C. | 340 | 360 |
| Pressure (gauge), MPa | 0.1 | 0.1 |
| Catalyst/alcohol ratio | 1 | 5 |
| WHSV, h⁻¹ | 1.0 | 1.5 |
| Product distribution, vol % | | |
| Ethylene | 95.79 | 98.32 |
| Propylene | 1.18 | 0.29 |
| Iso-butane | 0.72 | 0.15 |
| Total pentane | 0.45 | 0 |
| Total pentene | 0.25 | 0.31 |
| $C_6^+$ hydrocarbons | 0.54 | 0.53 |
| Conversion of ethanol, % | 99.1 | 99.5 |
| Selectivity to ethylene, % | 98 | 98.3 |
| Carbon base ethylene yield*, m % | 89.52 | 99.78 |

TABLE 2-continued

| | Example 1 | Example 2 |
|---|---|---|
| Catalyst type | CGP-1 | MMC-2 |
| Catalytic conversion of hydrocarbons | | |
| Reaction conditions | | |
| Temperature, ° C. | 500 | 550 |
| Pressure (gauge), MPa | 0.1 | 0.1 |
| Catalyst/oil ratio | 6 | 6 |
| Time on stream, s | 3 | 3 |
| Product distribution, wt % | | |
| Dry gas | 10.56 | 3.17 |
| LPG | 44.78 | 18.04 |
| Gasoline | 21.32 | 48.26 |
| Diesel oil | 6.89 | 18.73 |
| Heavy oil | 3.18 | 4.56 |
| Coke | 13.28 | 7.24 |

*Carbon base ethylene yield = Carbon content in the target product/carbon content in the ethanol feedstock

The invention claimed is:

1. A process for producing ethylene, characterized in that said process comprises the following steps:
   (1) contacting an ethanol feedstock with a first portion of a regenerated Y-zeolite containing catalyst to obtain a first product stream and to convert the first portion of the regenerated Y-zeolite containing catalyst into a coked catalyst in a first reactor, wherein the first portion of the regenerated Y-zeolite supplies heat to the conversion of the ethanol feedstock and wherein the first product stream is further separated in a first separation unit to obtain ethylene;
   (2) contacting a hydrocarbon feedstock with a second portion of the regenerated Y-zeolite containing catalyst to obtain a second product stream and convert the second portion of the regenerated Y-zeolite containing catalyst into a spent catalyst in a second reactor, wherein the second product stream is further separated in a second separation unit to obtain products comprising LPG, gasoline, and diesel oil;
   (3) regenerating a mixture of the coked catalyst and the spent catalyst in a regenerator by coke-burning to obtain the regenerated Y-zeolite containing catalyst, wherein the mixture comprises all or a portion of the coked catalyst and all or a portion of the spent catalyst; and
   (4) obtaining from the regenerated Y-zeolite containing catalyst the first portion of the regenerated Y-zeolite containing catalyst and the second portion of the regenerated Y-zeolite containing catalyst,
   wherein the hydrocarbon feedstock in step (2) is selected from the group consisting of vacuum gas oil, coker gas oil, deasphalted oil, hydrogenated bottom, atmospheric residuum, vacuum residuum and mixtures thereof,
   wherein the regenerated Y-zeolite containing catalyst comprises a Y-zeolite and one or more other molecular sieve and the weight ratio of said other molecular sieve to the Y-zeolite is less than or equal to 10.

2. The process according to claim 1, characterized in that the content of ethanol in said ethanol feedstock is 50-100% by weight.

3. The process according to claim 1, characterized in that the content of ethanol in said ethanol feedstock is 70-100% by weight.

4. The process according to claim 1, characterized in that the content of ethanol in said ethanol feedstock is 90-100% by weight.

5. The process according to claim 1, characterized in that the regenerated Y-zeolite containing catalyst further comprises inorganic oxides and/or clay.

6. The process according to claim 5, characterized in that said inorganic oxide is selected from the group consisting of alumina, silica, amorphous silica-alumina, and mixtures thereof, and the clay is kaolin clay and/or halloysite.

7. The process according to claim 1, characterized in that said other molecular sieve is one or more selected from meso porous zeolites, Beta-zeolites, and SAPO-molecular sieves.

8. The process according to claim 1, characterized in that the regenerated Y-zeolite containing catalyst comprises a Y-zeolite, a meso porous zeolite, an inorganic oxide, and clay.

9. The process according to claim 7 or 8, characterized in that said meso porous zeolite is chosen from ZRP series zeolites, ZSP series zeolites, ZSM series zeolites, or mixtures thereof.

10. The process according to claim 8, characterized in that the weight ratio of said meso porous zeolite to the Y-zeolite is 0.1-10, and the total weight of the meso porous zeolite and the Y-zeolite is 10-50% of total weight of the regenerated Y-zeolite containing catalyst.

11. The process according to claim 1, 8, or 10, characterized in that the Y-zeolite is selected from the group consisting of Y, HY, REY, REHY, USY, REUSY, and mixtures thereof.

12. The process according to claim 1, characterized in that the reaction conditions in the first reactor include a temperature of 200-450° C., a gauge pressure of 0-0.8 MPa, a weight ratio of the catalyst to the ethanol feedstock of 0.05-20, and a weight hourly space velocity of 0.05-10 $h^{-1}$.

13. The process according to claim 12, characterized in that the reaction temperature is 250-400° C. and the weight hourly space velocity is 0.1-5 $h^{-1}$.

14. The process according to claim 1, characterized in that the reaction conditions in the second reactor include a temperature of 400-700° C., a gauge pressure of 0-0.8 MPa, a weight ratio of the catalyst to the hydrocarbon feedstock of 1-30, and a contact time of 1-10 seconds.

15. The process according to claim 14, characterized in that the reaction temperature is 450-600° C.

16. The process according to claim 1, characterized in that the proportion of the coked catalyst generated in the first reactor subject to coke-burning regeneration is 0.5-100% by the total weight of the coked catalyst.

17. The process according to claim 1 or 16, characterized in that 0.5-99% by weight of the total coked catalyst generated in the first reactor enters the regenerator for coke-burning regeneration and the balance of the coked catalyst returns to the first reactor or enters the second reactor.

18. The process according to claim 1, characterized in that the proportion of the spent catalyst generated in the second reactor subject to coke-burning regeneration is 1-100% by the total weight of the spent catalyst.

19. The process according to claim 1 or 18, characterized in that 1-99% by the total weight of the spent catalyst generated in the second reactor enters the regenerator for coke-burning regeneration and the balance of the spent catalyst returns to the first reactor.

20. The process according to claim 1, characterized in that the regeneration in step (3) is one-stage regeneration or two-stage regeneration, and said regenerated catalyst is a partially regenerated catalyst and/or a full regenerated catalyst.

21. The process according to claim 1, characterized in that the first reactor and the second reactor are both catalyst-movable reactors, and are chosen from a fluidized bed, a riser, a descending transfer line reactor, a moving bed, a composite reactor of riser and fluidized bed, a composite reactor of riser and descending transfer line, a composite reactor of two or more risers, a composite reactor of two or more fluidized beds, a composite reactor of two or more descending transfer lines, and a composite reactor of two or more moving beds, wherein each of the above reactors comprise one or more reaction zones.

22. The process according to claim 1, characterized in that the first reactor is a fluidized bed, and the second reactor is a riser.

23. The process according to claim 21 or 22, characterized in that said riser is chosen from an iso-diameter riser, an equal-velocity riser, and various variable-diameter riser; and said fluidized bed is chosen from a fixed fluidized bed, a particulate fluidization bed, a bubbling bed, a turbulent bed, a quick bed, a transfer bed, and a dense-phase fluidized bed.

24. The process according to claim 1, characterized in that the regenerated catalyst is first cooled down to 200-450° C. before returning to the first reactor.

25. The process according to claim 24, characterized in that the cooling is carried out in a direct heat exchanger by directly contacting the regenerated catalyst with air having a relatively low temperature.

26. The process according to claim 1, characterized in that the weight ratio of the coked catalyst and the spent catalyst entering the regenerator for the coke-burning regeneration is less than or equal to 1.0.

* * * * *